(12) United States Patent
Shuk et al.

(10) Patent No.: US 11,892,370 B2
(45) Date of Patent: Feb. 6, 2024

(54) OXYGEN ANALYZER WITH PRESSURE COMPENSATION

(71) Applicant: Rosemount Inc., Shakopee, MN (US)

(72) Inventors: Pavel Shuk, Copley, OH (US); Dirk W. Bauschke, Shakopee, MN (US); David Loberg, Prior Lake, MN (US)

(73) Assignee: Rosemount Inc., Shakopee, MN (US)

( * ) Notice: Subject to any disclaimer, the term of this patent is extended or adjusted under 35 U.S.C. 154(b) by 58 days.

(21) Appl. No.: 17/482,973

(22) Filed: Sep. 23, 2021

(65) Prior Publication Data
US 2023/0086725 A1 Mar. 23, 2023

(51) Int. Cl.
*G01M 15/10* (2006.01)
*G01N 33/00* (2006.01)
*G01N 27/409* (2006.01)

(52) U.S. Cl.
CPC ........ *G01M 15/106* (2013.01); *G01N 27/409* (2013.01); *G01N 33/0062* (2013.01); *G01N 33/0073* (2013.01)

(58) Field of Classification Search
CPC .. F23N 5/006; F23N 2037/26; F23N 2037/28; F02D 2200/703; F02D 41/123; F02D 41/1402; F02D 41/1448; F02D 41/1456; G01M 15/106; G01M 15/104; G01N 27/409; G01N 33/0062; G01N 33/0073; G01N 27/41; G01N 27/419; F02B 77/086; F24F 2011/0028
See application file for complete search history.

(56) References Cited

U.S. PATENT DOCUMENTS

| 9,448,201 | B2 | 9/2016 | Kramer et al. |
| 2013/0066564 | A1 | 3/2013 | Forsyth |
| 2014/0150760 | A1 | 6/2014 | Surnilla et al. |

(Continued)

FOREIGN PATENT DOCUMENTS

JP    H06273370 A    9/1994

OTHER PUBLICATIONS

Pressure Compensated Oxygen Probes (Zirconia), Yokogawa technical note, Mar. 17, 2009, 5 pages.
(Continued)

*Primary Examiner* — Eric S. McCall
*Assistant Examiner* — Timothy P Graves
(74) *Attorney, Agent, or Firm* — Christopher R. Christenson; Kelly, Holt & Christenson, P.L.L.C.

(57) ABSTRACT

A process oxygen analyzer includes a process probe extendible into a flow of process combustion exhaust, the process probe having an oxygen sensor measurement cell. Measurement circuitry is coupled to the oxygen sensor measurement cell and configured to obtain a non-corrected indication of oxygen concentration relative to a combustion process based on an electrical characteristic of the oxygen sensor measurement cell. A controller is operably coupled to the measurement circuitry and is configured to obtain an indication of process pressure and selectively provide a corrected oxygen concentration output based on non-corrected indication of oxygen concentration and the indication of process pressure. A method of providing a process oxygen concentration using a process oxygen analyzer coupled to an industrial combustion process is also disclosed.

13 Claims, 8 Drawing Sheets

(56) References Cited

U.S. PATENT DOCUMENTS

| | | | | |
|---|---|---|---|---|
| 2014/0290329 A1* | 10/2014 | Kramer | ............. | G01N 27/4175 |
| | | | | 73/1.57 |
| 2014/0290347 A1* | 10/2014 | Higuchi | ............. | G01M 15/106 |
| | | | | 73/114.71 |
| 2016/0245516 A1* | 8/2016 | Sutton | ................. | G01N 1/2258 |
| 2017/0003246 A1* | 1/2017 | Shuk | ................. | G01N 27/4075 |

OTHER PUBLICATIONS

International Search Report and Written Opinion for PCT/US2022/043970, dated Jan. 20, 2023, 11 pages.

* cited by examiner

OXYGEN ANALYZER WITH PRESSURE COMPENSATION

BACKGROUND

Industrial process industries primarily rely upon energy sources that include one or more combustion processes. Such combustion processes include operation of a furnace or boiler to generate energy from combustion, which is then used for the process. While combustion provides relatively low-cost energy, its use is typically regulated and combustion efficiency is sought to be maximized. Accordingly, one goal of the process management industry is to reduce the production of greenhouse gases by maximizing combustion efficiency of existing furnaces and boilers.

In-situ or in-process flue gas analyzers are commonly used for the monitoring, optimization, and control of combustion processes. Typically, these analyzers employ sensors that are heated to relatively high temperatures and are operated directly above, or near, the furnace or boiler combustion zone. In-situ flue gas analyzers, such as those sold under the trade designation Oxymitter or Model 6888 In-situ Flue Gas Oxygen Transmitter available from Rosemount, Inc. (a business unit of Emerson Automation Solutions), often employ Zirconia-based electrochemical oxygen sensors heated to an elevated temperature.

SUMMARY

A process oxygen analyzer includes a process probe extendible into a flow of process combustion exhaust, the process probe having an oxygen sensor measurement cell. Measurement circuitry is coupled to the oxygen sensor measurement cell and configured to obtain a non-corrected indication of oxygen concentration relative to a combustion process based on an electrical characteristic of the oxygen sensor measurement cell. A controller is operably coupled to the measurement circuitry and is configured to obtain an indication of process pressure and selectively provide a corrected oxygen concentration output based on non-corrected indication of oxygen concentration and the indication of process pressure. A method of providing a process oxygen concentration using a process oxygen analyzer coupled to an industrial combustion process is also disclosed.

DETAILED DESCRIPTION OF ILLUSTRATIVE EMBODIMENTS

Zirconia-based electrochemical oxygen sensors are widely used in the industrial applications for the oxygen measurements. A significant portion of such industrial applications is for oxygen measurement of flue gas that vents to the atmosphere. In this application, the differential pressure between the process and ambient is much less than 12 inches of water column (0.43 psi). An in-situ oxygen analyzer (shown in FIG. 1) in such an environment will function for many years, controlling oxygen level in the flue gas after combustion. The stoichiometric point with the highest efficiency and the lowest emissions would be very difficult to achieve in the real-world combustion because of the imperfect fuel/air uniformity as well as the fuel energy density and fuel/airflow variation. Typical flue gas oxygen excess concentration is approximately 2-3% for gas burners, and 3-6% for boilers and oil burners. The best operating point is believed to be similar between 1 and 6% excess oxygen concentration. This optimum operating point depends on boiler load and firing rates. A function generator curve is typically developed from test data to assign the ideal oxygen trimming control point based on firing rate index, fuel or steam flow.

Figure 1:
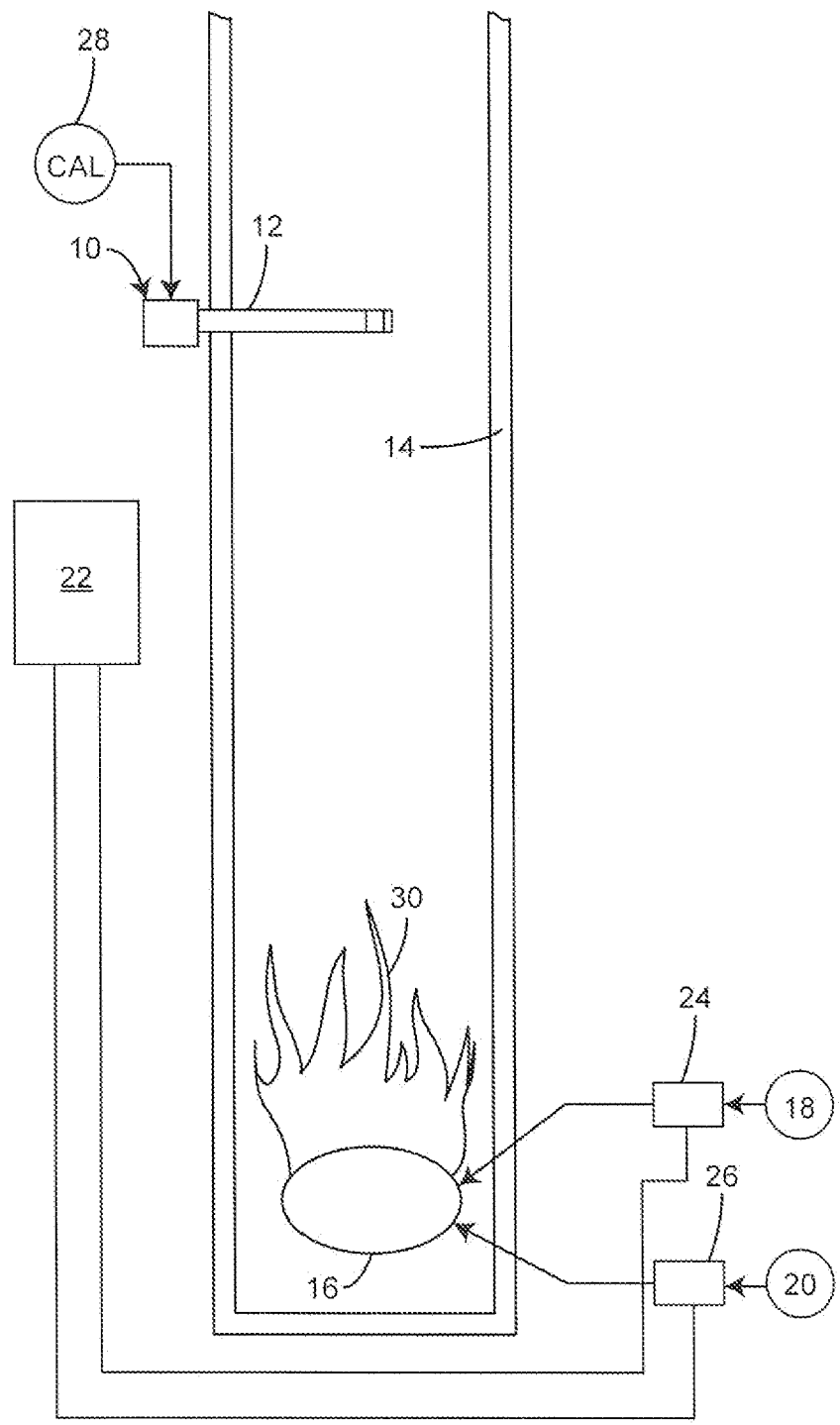
FIG. 1 is a diagrammatic view of an in-situ analyzer with which embodiments of the present invention are particularly useful.

FIG. 1 is a diagrammatic view of a combustion process using an in-situ analyzer. Transmitter 10 can be any suitable analyzer including the Model 6888 Flue Gas Oxygen Transmitter listed above. Transmitter 10 includes a probe assembly 12 that is disposed within a stack or flue 14 and measures at least one parameter (such as oxygen concentration) related to combustion occurring at burner 16. Typically, transmitter 10 is an oxygen transmitter, but can be any device that measures any suitable parameter related to the combustion process. Burner 16 is operably coupled to a source of air or oxygen 18 and a source 20 of combustible fuel. Each of sources 18 and 20 is preferably coupled to burner through a valve of some sort to deliver a controlled amount of oxygen and/or fuel to burner 16 in order to control the combustion process. Transmitter 10 measures the amount of oxygen in the combustion exhaust flow and provides an indication of the oxygen level to combustion controller 22, which controls one or both of valves 24, 26 to provide closed-loop combustion control. Transmitter 10 includes an oxygen sensor that typically employs a zirconia sensor to provide an electrical signal indicative of oxygen concentration, content or percentage in the flue gas.

When the pressure differential for the in-situ oxygen analyzer increases beyond 12 inches of water column (0.43 psi), the sensor signal and information become less accurate and reliable. The response of the sensor to the differential oxygen concentrations with fixed partial pressure on the reference electrode (e.g., using air), can be calculated using the well-known Nernst equation set forth below:

$$EMF = \frac{RT}{4F} * \ln\frac{P_{process}}{P_{ref}} + C = 0.0496 * T * \log\frac{P_{process}}{P_{ref}} + C$$

In the equation set forth above, C is the constant related to the reference/process sides temperature variation and the thermal junctions in the oxygen probe, R is the universal gas constant, T is the process temperature in degrees Kelvin and F is the Faraday constant.

Unfortunately, in many combustion applications, pressure variations in the process might compromise oxygen regulation and control, bringing significant (for example between 0.7 and 2.55%) oxygen reading error in the measurement. In accordance with embodiments set forth below, a pressure sensor is disposed proximate the measurement cell in order to measure process pressure acting on the measurement cell. This process pressure measurement is then provided to a controller, or other suitable computation circuitry, to adjust and/or compensate the oxygen sensor output based on the process pressure.

Figure 2:
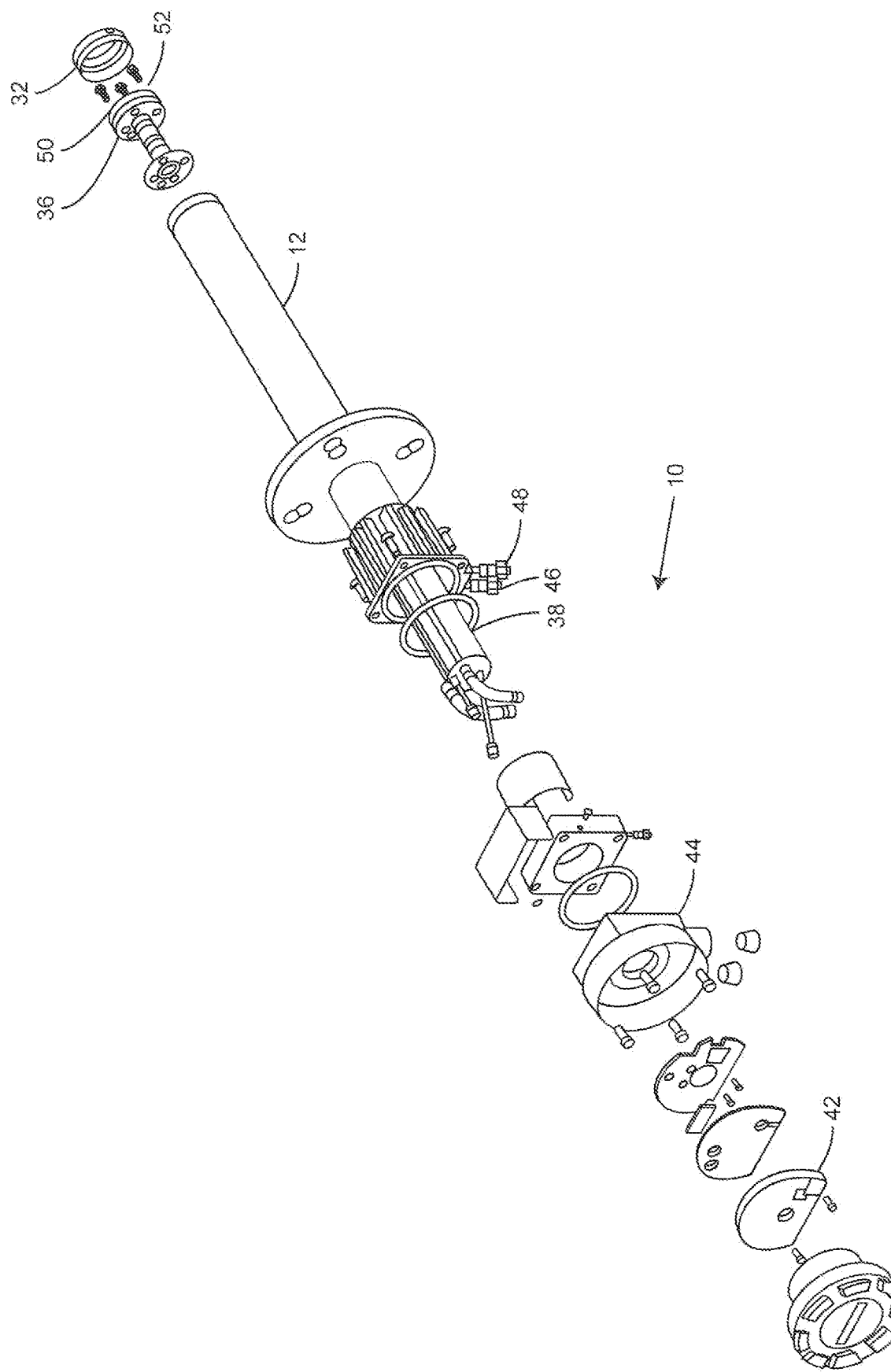
FIG. 2 is a diagrammatic exploded view of a process analytic oxygen analyzer in accordance with an embodiment of the present invention.

FIG. 2 is a diagrammatic view of an in-situ process combustion oxygen analyzer in accordance with an embodiment of the present invention. Probe assembly 12 is generally configured to house a sensor core assembly which includes diffuser 32 disposed next to measurement cell 36. Measurement cell 36 and heater assembly 38 are electrically coupled to electronic circuitry contained on electronics board 42 in housing 44. Transmitter 10 also includes a plurality of gas inlets 46 and 48 to receive reference air and calibration gas, respectively.

As illustrated in FIG. 2, transmitter 10 includes a pressure sensor 50 that is fluidically coupled to chamber or region 52 between measurement cell 36 and diffuser 32. In the embodiment shown in FIG. 2, pressure sensor 50 is disposed to measure process pressure during normal operation. Pressure sensor 50 may be any suitable type of pressure sensor including a deflectable diaphragm, capacitance-based pressure sensor, a deflectable diaphragm strain gauge, resistance-based pressure sensor, or any other suitable type of pressure sensor. However, the pressure sensor should be configured for exposure to the relatively low pressures and relatively high temperatures of operating in the flue-gas environments.

While the embodiment described above provides an oxygen sensor measuring cell and pressure sensor in close proximity such that the pressure sensor provides an indication of process pressure proximate the measurement cell, embodiments described herein can also receive process pressure measurement information from an external device, such as a process pressure transmitter, and use the received process pressure information to provide a compensated oxygen sensor output.

Figure 3:
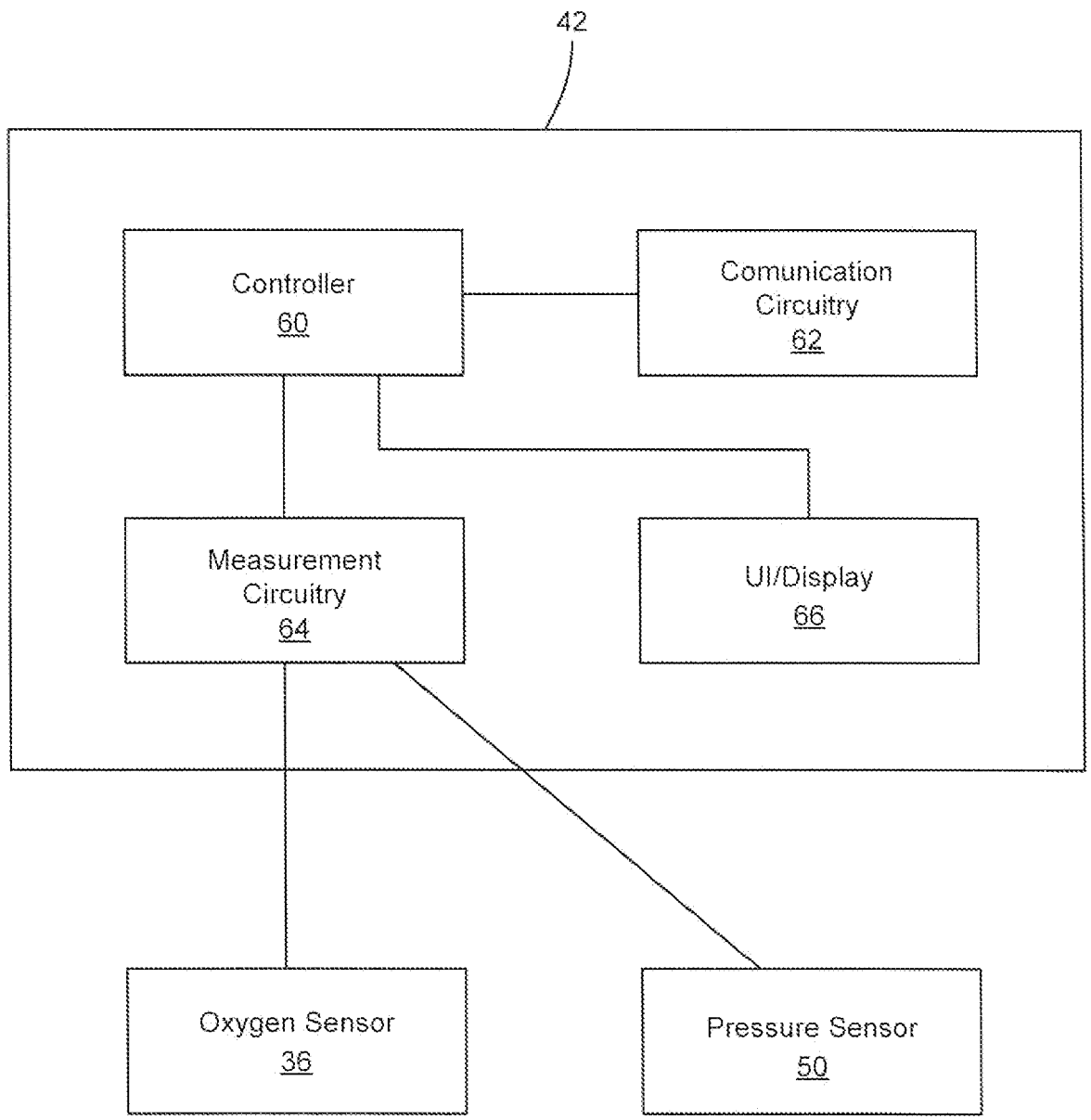
FIG. 3 is a block diagram of a process analytic oxygen analyzer in accordance with an embodiment of the present invention.

FIG. 3 is a block diagram of electronics board 42 of process analytic oxygen transmitter 10 in accordance with an embodiment of the present invention. FIG. 3 indicates additional components of electronics board 42. Specifically, electronic circuitry on electronics board 42 includes controller 60 coupled to communication circuitry 62 and measurement circuitry 64. Controller 60 is also coupled to UI/display module 66. Controller 60 may be any suitable device that executes a sequence of instructions to perform one or more control functions. In one embodiment, controller 60 is a microprocessor.

Communication module 62 is coupled to controller 60 and allows controller 60 to communicate with one or more process devices, such as combustion controller 22 (shown in FIG. 1) in accordance with a wired process industry standard communication protocol. Examples of such protocols include the Highway Addressable Remote Transducer HART® Protocol and the FOUNDATION™ Fieldbus protocol. Additionally, or alternatively, communication module 62 may be a wireless communication module allowing controller 60 to communicate in accordance with a wireless process communication protocol, such as IEC 62591. In embodiments where controller 60 uses process pressure information received via another process variable transmitter (i.e., pressure transmitter), communication module 62 provides such communication to controller 60 in order to allow controller 60 to obtain process pressure information.

Measurement circuitry 64, in one embodiment, includes an analog-to-digital converter configured to measure an electrical characteristic of sensors connected thereto. As shown, measurement circuitry 64 is coupled to oxygen sensor 36 in order to obtain a non-corrected oxygen sensor signal. Additionally, measurement circuitry 64 is also coupled to pressure sensor 50 to measure an electrical characteristic, such as capacitance, of pressure sensor 50 that is indicative of process pressure and provide a digital indication of such to controller 60. Measurement circuitry 64 may also include suitable amplification, filtering, and/or linearization circuitry as desired.

Controller 60 receives information indicative of the non-corrected oxygen sensor signal and the process pressure and uses a known relationship between process pressure and oxygen sensor signal error to correct the non-corrected oxygen sensor signal based on the measured process pressure. Note, in embodiments where the process pressure information is received from an external source, such as a process pressure transmitter or via a user entering process pressure information via UI/Display module 66, the pressure sensor may be omitted.

Figure 4:
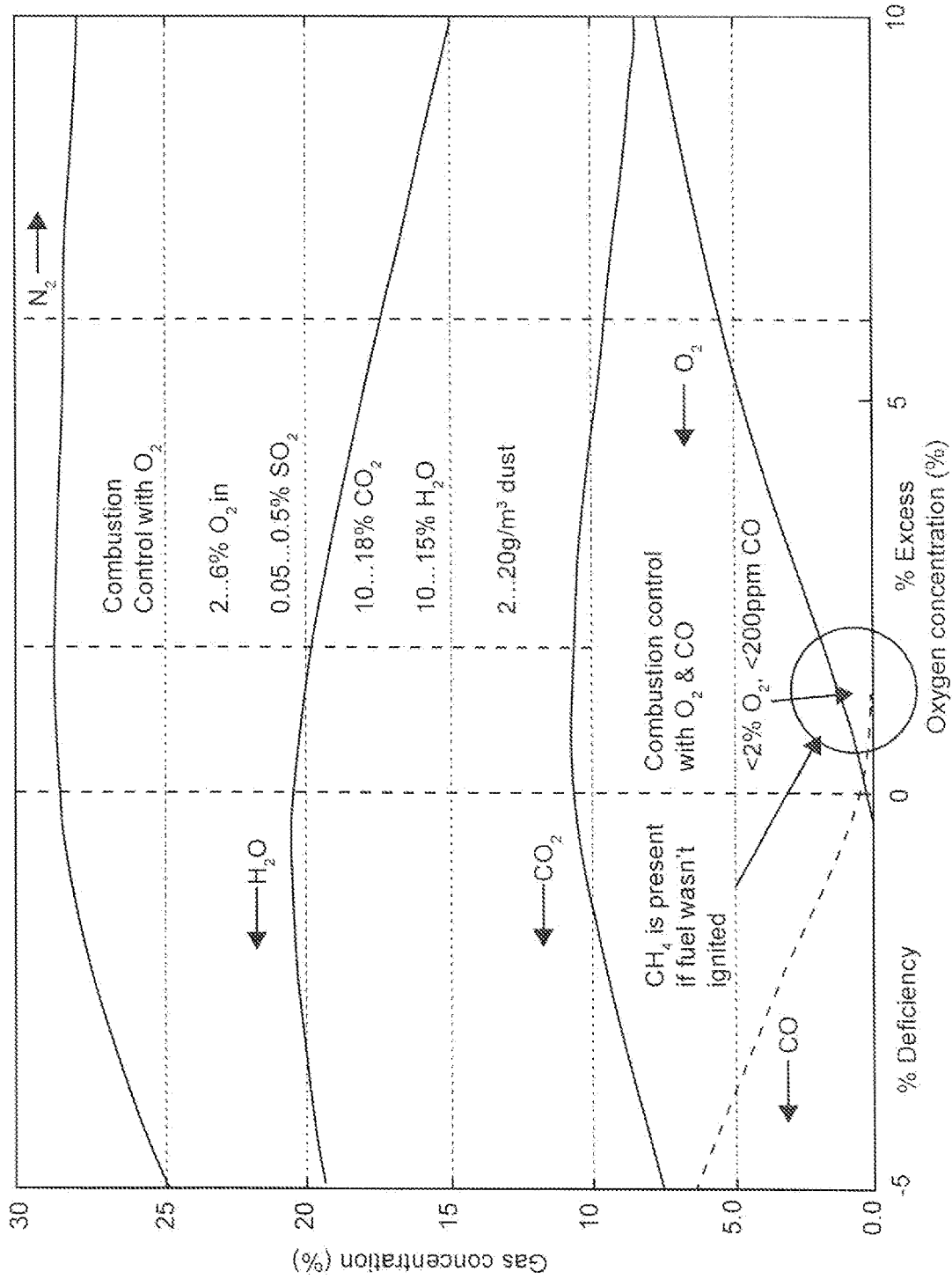
FIG. 4 is a chart of gas concentration vs. oxygen concentration showing combustion control.

FIG. 4 is a chart of gas concentration vs. oxygen concentration showing combustion control. FIG. 4 is an example of a function generator curve that is typically developed from test data to assign the ideal oxygen trimming control point based on the firing rate index, fuel, or steam flow. As set forth above, in many combustion applications, pressure variations in the process may undesirably affect the oxygen sensor signal.

Figure 5:
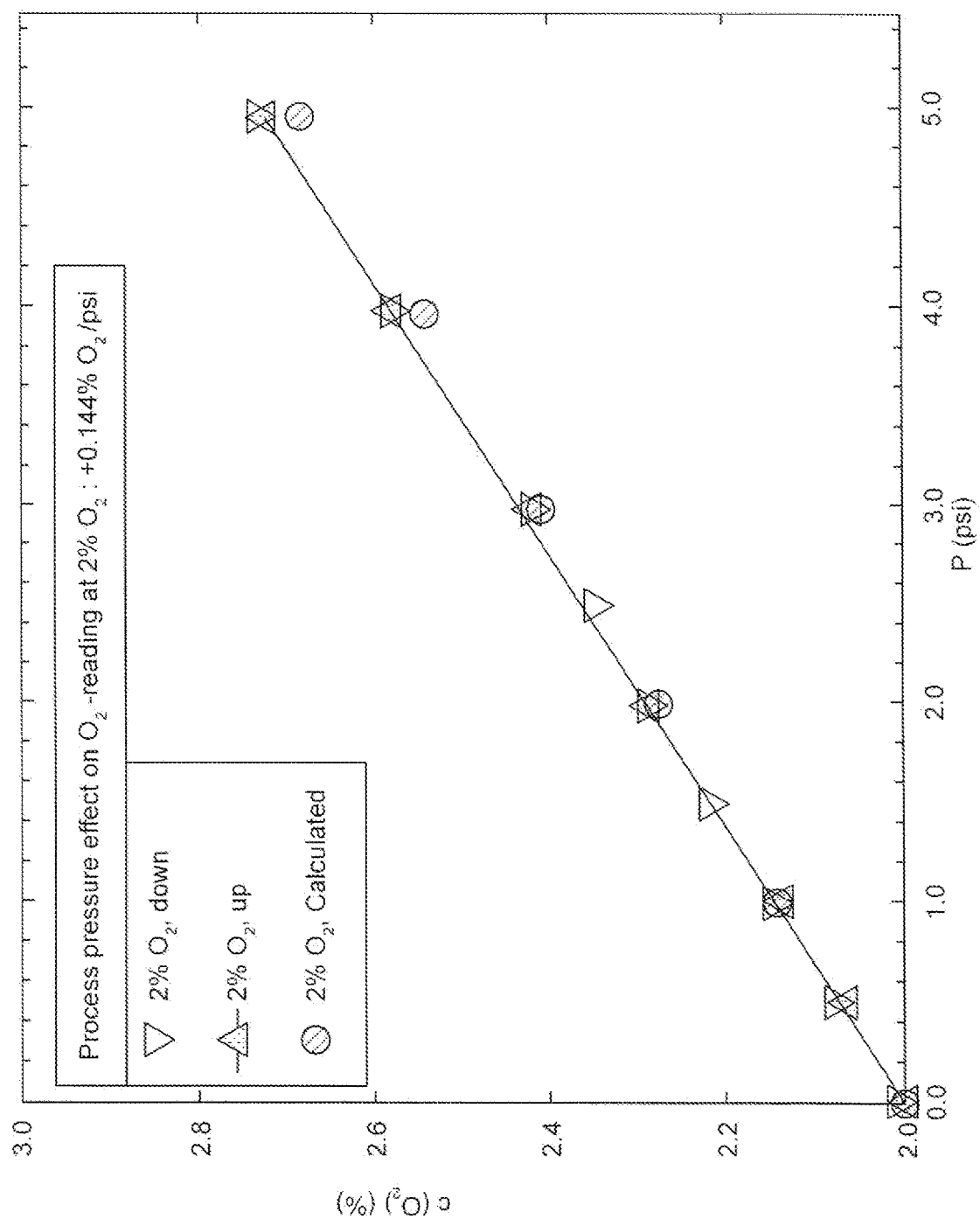
FIG. 5 is a graph of the effects of oxygen concentration error as a function of pressure for oxygen concentrations ranging from 2.0% to 3.0%.

FIG. 5 is a chart illustrating process pressure effect on oxygen sensor reading at 2.0-2.7% oxygen concentration. As shown, for higher levels of oxygen concentration (i.e., 2.65%) and relatively higher pressures (e.g., 5 PSI) the error can become significant.

Figure 6:
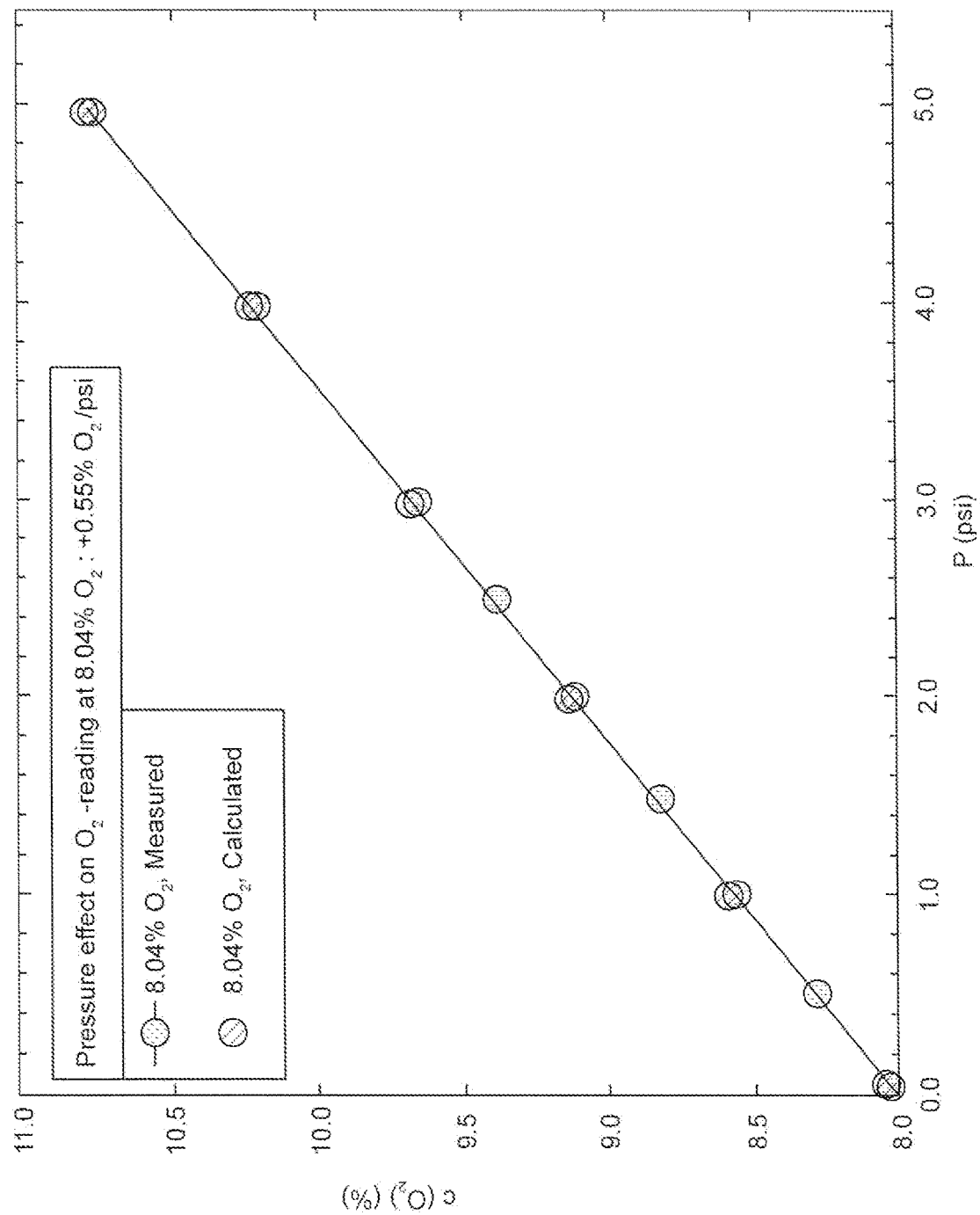
FIG. 6 is a graph of the effects of oxygen concentration error as a function of pressure for oxygen concentrations ranging from 8.0% to 11.0%.

FIG. 6 is a chart illustrating the pressure effect on oxygen sensor analyzer reading at higher oxygen concentration (8.0%-10.75%). In this example, the relatively higher oxygen percent concentration provides less error than at the lower (e.g., approximately 2%) concentrations shown in FIG. 5.

Figure 7:
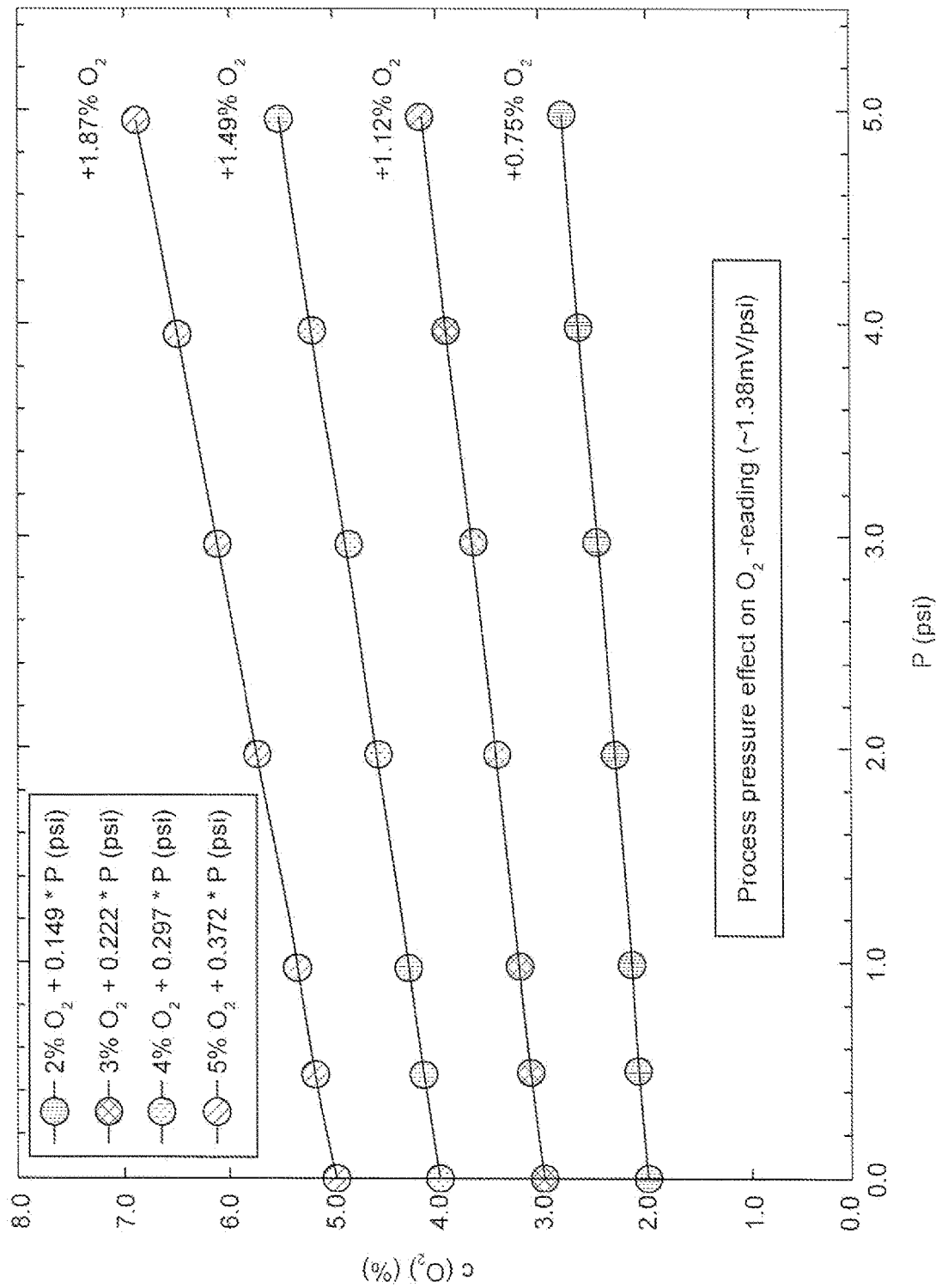
FIG. 7 is a graph of the effects of oxygen concentration error as a function of pressure for various oxygen concentrations.

FIG. 7 is a chart showing various oxygen concentrations (2%, 3%, 4% and 5%), at various pressures ranging from 0-5 psi. The process pressure effect on the oxygen sensor reading is approximately 1.38 mV per psi. There are certain processes where the process is operated under pressure, and accurate oxygen measurement is still required. In the past, some pressure balancing systems were employed to negate effects of the pressure imbalance. However, such approaches were disfavored due to the requirement for hazardous location approvals. In accordance with embodiments herein, for a pressurized process (i.e., greater than 0.5 psi) controller 60 applies pressure compensation to the non-corrected oxygen sensor measurement according to the relationship illustrated in FIG. 7. The pressure-induced error illustrated in FIG. 7 was obtained experimentally using a standard oxygen cell. This correlation would be similar for other Zirconia-based oxygen analyzers, but it may not be an exact match due to construction differences. Accordingly, some experimentation may be required in order to relate the effects of pressure on a given Zirconia-based oxygen sensor. However, once such relationship is obtained, the relationship such as the linear relationship shown in FIG. 7 (i.e., 1.38 mV per psi) can simply be entered into the controller (e.g. during manufacture of the system or upon testing/calibrating a particular sensor with the system) in order to provide the compensated oxygen sensor output. Further, for process pressure less than the selected threshold (i.e., 0.5 psi), controller 60 may simply provide a non-compensated output using the non-corrected oxygen sensor signal and the Nernst equation. Thus, in accordance with at least one embodiment described herein, controller 60 of oxygen analyzer 10 can receive an indication of process pressure (either using a local pressure sensor disposed proximate a measurement cell or using process communication) and determine whether the process pressure exceeds a threshold (i.e., 0.5 psi) in order to determine whether to apply a pressure-based compensation. As set forth above, in some embodiments, the process pressure measurement could even be entered into the oxygen analyzer using user interface module/display 66.

While the pressure used for embodiments described herein could be a continuously-updated pressure value, it does not need to be so. This is because the T90 response time for the oxygen sensor is generally on the order of minutes, not seconds. Thus, the pressure may simply be a one-time entry and only updated each time the oxygen analyzer is calibrated.

Figure 8:
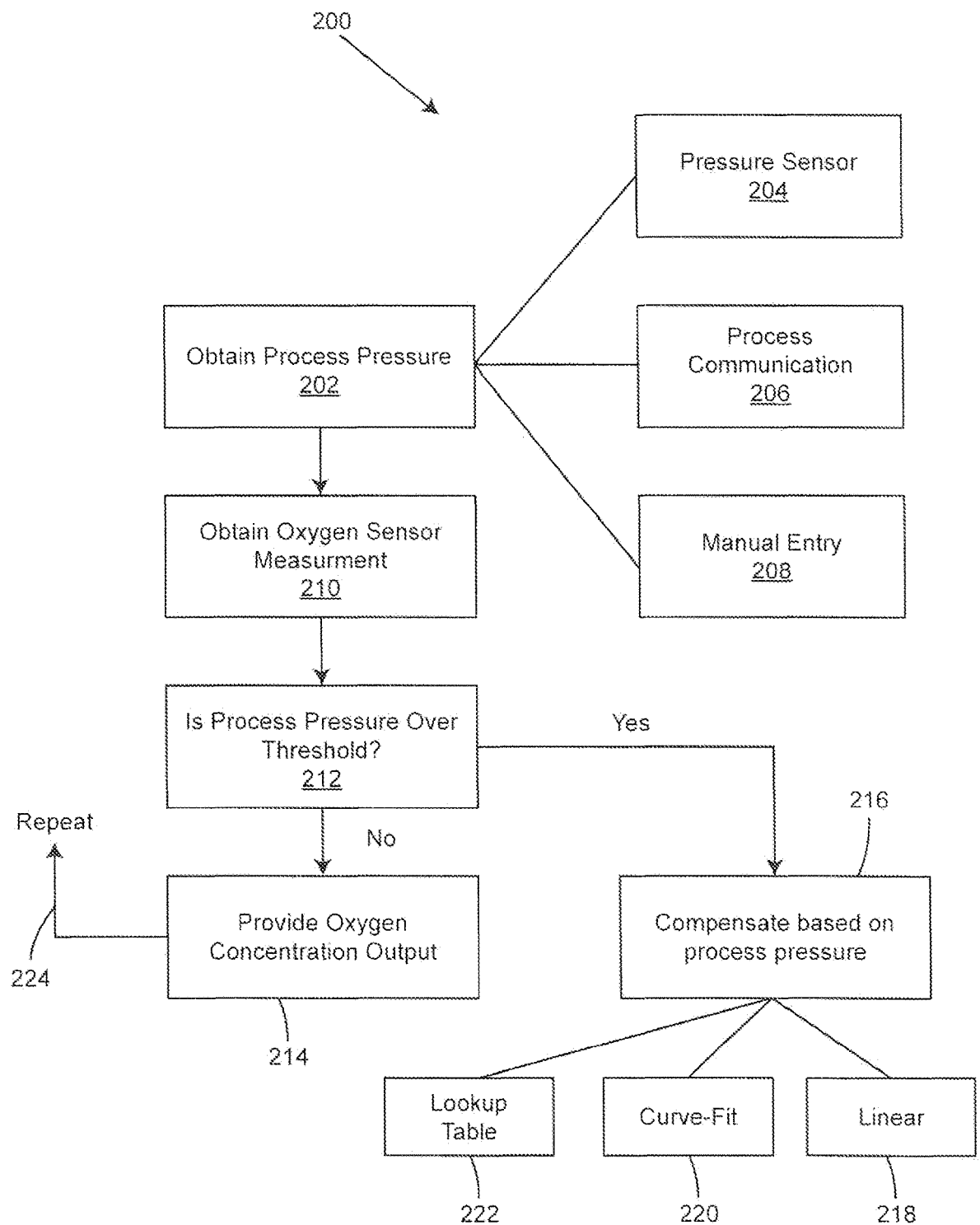
FIG. 8 is a flow diagram of a method of providing a pressure compensated oxygen output in accordance with an embodiment of the present invention.

FIG. 8 is a flow diagram of a method of providing a pressure compensated oxygen output in accordance with an embodiment of the present invention. Method 200 begins at block 202 where process pressure is obtained. The process pressure may be obtained from a pressure sensor disposed in a probe of the oxygen analyzer (e.g., as shown in FIG. 2) as indicated at reference numeral 204. Additionally, or alternatively, the process pressure may be obtained from other sources as well. For example, the process pressure may be obtained from a remote process device using process communication 206 and/or entered into the oxygen analyzer by a user via a suitable user interface, such as UI/display module 66 (shown in FIG. 3). Next, at block 210, a non-corrected oxygen sensor measurement is obtained from an oxygen sensor located in or proximate the process. At block 212, the process pressure obtained at block 202 is compared to a pre-defined (i.e., 0.5 psi) threshold to determine whether the process pressure is at or above the pre-defined threshold. If not, control passes to block 214 where the non-corrected oxygen sensor signal is simply used to provide an oxygen concentration output using the Nernst equation set forth above.

If the process pressure is determined, at block 212, to be at or above the pre-defined threshold, then control passes to block 216, where a pressure-based compensation is applied to the non-corrected oxygen sensor signal. This compensation may add a compensation value that scales with the process pressure to the non-corrected oxygen sensor signal. In one example, the compensation value is a voltage value that is obtained by multiplying the process pressure with a linear compensation value (e.g., 1.38 mV/psi), as indicated at reference numeral 218. In other embodiments, more complex relationships between the process pressure (as well as other variables) and the compensation value may be modelled using a curve-fit, as indicated at reference numeral 220. Further, in order to reduce computational complexity, such relationships may also be modelled using a lookup table, as indicated at reference numeral 222. The corrected oxygen sensor signal is then used by the controller, at block 214, to provide the oxygen concentration output. The method repeats, as indicated at reference numeral 224. Note, the iteration can return to block 202 to obtain a process pressure in substantially real-time. However, since the process pressure does not need to be updated as frequently as the oxygen sensor measurement, the iteration can return to block 210 for a certain number of cycles or time before the iteration obtains an updated process pressure.

Although the present invention has been described with reference to preferred embodiments, workers skilled in the art will recognize that changes may be made in form and detail without departing from the spirit and scope of the invention.

What is claimed is:

1. A process oxygen analyzer comprising:
a process probe extendible into a flow of process combustion exhaust, the process probe having an oxygen sensor measurement cell;
measurement circuitry coupled to the oxygen sensor measurement cell and configured to obtain a non-corrected indication of oxygen concentration relative to a combustion process based on an electrical characteristic of the oxygen sensor measurement cell;
a controller operably coupled to the measurement circuitry, the controller being configured to obtain an indication of process pressure and selectively provide a corrected oxygen concentration output based on non-corrected indication of oxygen concentration and the indication of process pressure
a user interface (UI)/display module operably coupled to the controller; and
wherein the controller is configured to obtain the indication of process pressure via the UI/display module.

2. The process oxygen analyzer of claim 1, wherein the controller is configured to compare the process pressure to a pre-defined threshold and selectively provide the corrected oxygen concentration output based on whether the indication of process pressure exceeds the pre-defined threshold.

3. The process oxygen analyzer of claim 2, wherein the pre-defined threshold is approximately 0.5 psi.

4. The process oxygen analyzer of claim 1, and further comprising communication circuitry coupled to the controller, the communication circuitry being configured to communicate in accordance with a process industry standard communication protocol.

5. The process oxygen analyzer of claim 1, wherein the controller is configured to generate the corrected oxygen concentration output based on a linear compensation factor that relates error of the non-corrected indication of oxygen concentration to process pressure.

6. The process oxygen analyzer of claim 1, wherein the oxygen sensor measurement cell includes a zirconia oxygen sensor.

7. A method of providing a process oxygen concentration using a process oxygen analyzer coupled to an industrial combustion process, the method comprising:
obtaining an indication of process pressure;
obtaining a non-corrected indication of oxygen concentration using a measurement cell coupled to the industrial combustion process;
comparing the indication of process pressure to a pre-defined threshold and providing a corrected oxygen concentration output if the process pressure exceeds the pre-defined threshold and providing a non-corrected oxygen concentration output it the process pressure does not exceed the pre-defined threshold; and
wherein providing a corrected oxygen concentration output includes multiplying the indication of process pressure by a known compensation factor that relates error of the non-corrected indication oxygen concentration to process pressure.

8. The method of claim 7, wherein obtaining the indication of process pressure includes employing measurement circuitry of the process oxygen analyzer to determine an electrical characteristic of a pressure sensor disposed to measure the process pressure.

9. The method of claim 7, wherein obtaining the indication of process pressure includes receiving the indication from a remote device using process communication circuitry of the process oxygen analyzer.

10. The method of claim 7, wherein obtaining the indication of process pressure includes receiving the indication from a user interface (UI)/display module of the process oxygen analyzer.

11. The method of claim 7, wherein the pre-defined threshold is 0.5 psi.

12. The method of claim 7, wherein the method iterates.

13. The method of claim 12, wherein the iterating method obtains the non-corrected indication of oxygen concentration more frequently than the indication of process pressure.

\* \* \* \* \*